(12) United States Patent
Li et al.

(10) Patent No.: US 7,248,910 B2
(45) Date of Patent: Jul. 24, 2007

(54) PHYSIOLOGICAL PARAMETER MONITORING SYSTEM AND SENSOR ASSEMBLY FOR SAME

(75) Inventors: Luya Li, Coquitlam (CA); Rakesh Kumar Sethi, Vancouver (CA); Ming Sun, New Westminster (CA)

(73) Assignee: CardioDigital Limited, East Lothian (GB)

( * ) Notice: Subject to any disclaimer, the term of this patent is extended or adjusted under 35 U.S.C. 154(b) by 353 days.

(21) Appl. No.: 10/493,246

(22) PCT Filed: Oct. 22, 2002

(86) PCT No.: PCT/CA02/01589

§ 371 (c)(1),
(2), (4) Date: Apr. 21, 2004

(87) PCT Pub. No.: WO03/034911

PCT Pub. Date: May 1, 2003

(65) Prior Publication Data

US 2004/0267103 A1 Dec. 30, 2004

Related U.S. Application Data

(60) Provisional application No. 60/330,425, filed on Oct. 22, 2001, provisional application No. 60/347,870, filed on Jan. 15, 2002.

(51) Int. Cl.
*A61B 5/00* (2006.01)
*A61B 5/02* (2006.01)

(52) U.S. Cl. .................. 600/323; 600/324; 600/310; 600/485

(58) Field of Classification Search ............... 600/300, 600/323, 481, 310, 324, 485
See application file for complete search history.

(56) References Cited

U.S. PATENT DOCUMENTS

| | | | | |
|---|---|---|---|---|
| 5,720,293 | A * | 2/1998 | Quinn et al. | 600/505 |
| 5,904,708 | A | 5/1999 | Goedeke | |
| 5,987,343 | A * | 11/1999 | Kinast | 600/323 |
| 6,230,059 | B1 | 5/2001 | Duffin | |
| 6,298,255 | B1 * | 10/2001 | Cordero et al. | 600/372 |
| 6,308,089 | B1 * | 10/2001 | von der Ruhr et al. | 600/338 |
| 6,515,273 | B2 * | 2/2003 | Al-Ali | 250/214.1 |
| 6,553,241 | B2 * | 4/2003 | Mannheimer et al. | 600/323 |
| 6,676,600 | B1 * | 1/2004 | Conero et al. | 600/438 |

* cited by examiner

*Primary Examiner*—Eric F. Winakur
(74) *Attorney, Agent, or Firm*—Oyen Wiggs Creen & Mutala LLP

(57) ABSTRACT

A detachable sensor assembly for use in monitoring a physiological parameter of a subject includes an information containing circuit and a timer. The sensor assembly stores time varying information in the information containing circuit. The information may include cumulative use times for the detachable sensor assembly and/or for components in the detachable sensor assembly.

22 Claims, 4 Drawing Sheets

PHYSIOLOGICAL PARAMETER MONITORING SYSTEM AND SENSOR ASSEMBLY FOR SAME

CROSS REFERENCE TO RELATED APPLICATIONS

This application claims the benefit of the filing dates of U.S. patent application Ser. No. 60/330,425 filed on 22 Oct. 2001 and entitled PHYSIOLOGICAL PARAMETER MONITORING SYSTEM AND SMART SENSOR ASSEMBLY FOR SAME and application No. 60/347,870 filed on 15 Jan., 2002 and entitled SMART SENSOR ASSEMBLY FOR MONITORING PHYSIOLOGICAL PARAMETERS, both of which are hereby incorporated herein by reference.

TECHNICAL FIELD

This application relates to medical devices, and in particular to systems for monitoring one or more physiological parameters of a subject. The invention relates to such systems which include one or more detachable sensors. The sensors may include pulse oximetry sensors and may be connected to deliver signals to a monitoring device by way of a cord comprising one or more signal transmission lines.

BACKGROUND

Modern medical devices have sensors for measuring various physiological parameters of patients. The inventor has determined that there is a need for automated systems which facilitate the management of such sensors.

SUMMARY OF THE INVENTION

This invention provides sensor assemblies which incorporate circuits which store information relating to the sensor assemblies. Sensor assemblies according to some aspects of the invention include processors for processing data.

One aspect of the invention provides detachable sensor assemblies for supplying signals to devices for monitoring physiological parameters of subjects. The detachable sensor assemblies comprise: a sensor; an information containing circuit; a timer; and, a connector comprising one or more signal conductors connected to carry information from the sensor and information from the information containing circuit to a device for monitoring a physiological parameter. The information containing circuit is configured to store time-varying information in response to timing signals from the timer and to transmit the time varying information by way of the connector. In sensor assemblies according to specific embodiments of the invention the time varying information comprises one or more of:

a cumulative time during which power has been applied to the sensor;
a cumulative time during which an active component in the sensor has been operating;
a cumulative time during which the sensor has been acquiring data from a subject;
a cumulative time since a sensor reset;
a cumulative time since a sensor error;
a cumulative time since the sensor was calibrated; and,
a cumulative time since an interruption in a signal detected by the sensor.

Another aspect of the invention provides a system for determining a value of a physiological parameter comprising a detachable sensor assembly as described above connected to a monitoring device. The monitoring device may be configured to: retrieve a first instance of the time varying value from the information containing circuit at a first time; store the first instance of the time varying value in a memory; retrieve a second instance of the time varying value from the information containing circuit at a second time later than the first time; and, compare the first and second instances of the time varying value to a difference between the first and second times. The time varying value may comprise a cumulative use time for a component in the detachable sensor assembly and the monitoring device may be configured to energize the component at or before the first time.

Another aspect of the invention provides apparatus for monitoring a physiological parameter of a subject. The apparatus comprises a monitoring device comprising stored information identifying one or more acceptable sensor combinations, each of the acceptable sensor combinations comprising a plurality of sensor locations required for the determination of a physiological parameter; and, a plurality of sensors detachably connected to the monitoring device. Each of the sensors is intended for application to a different location on a subject's anatomy. Each of the sensors comprises a circuit containing stored information indicating the intended location for the sensor. The monitoring device comprises a processor connected to retrieve the stored information from each of the plurality of sensors, and to determine from the retrieved stored information whether the plurality of sensors includes all sensors of at least one of the acceptable sensor combinations.

A further aspect of the invention provides a method for operating a detachable sensor assembly comprising a sensor for supplying a signal to a monitoring device for monitoring a physiological parameter of a subject. The method comprises determining in the detachable sensor assembly a time varying value; storing the time varying value in a data store on the detachable sensor assembly a time varying value; and, transmitting the time varying value to a monitoring device detachably connected to the detachable sensor assembly.

Further aspects of this invention and features of specific embodiments of this invention are described below.

BRIEF DESCRIPTION OF THE DRAWINGS

In drawings which illustrate non-limiting embodiments of the invention.

DESCRIPTION

Figure 1:
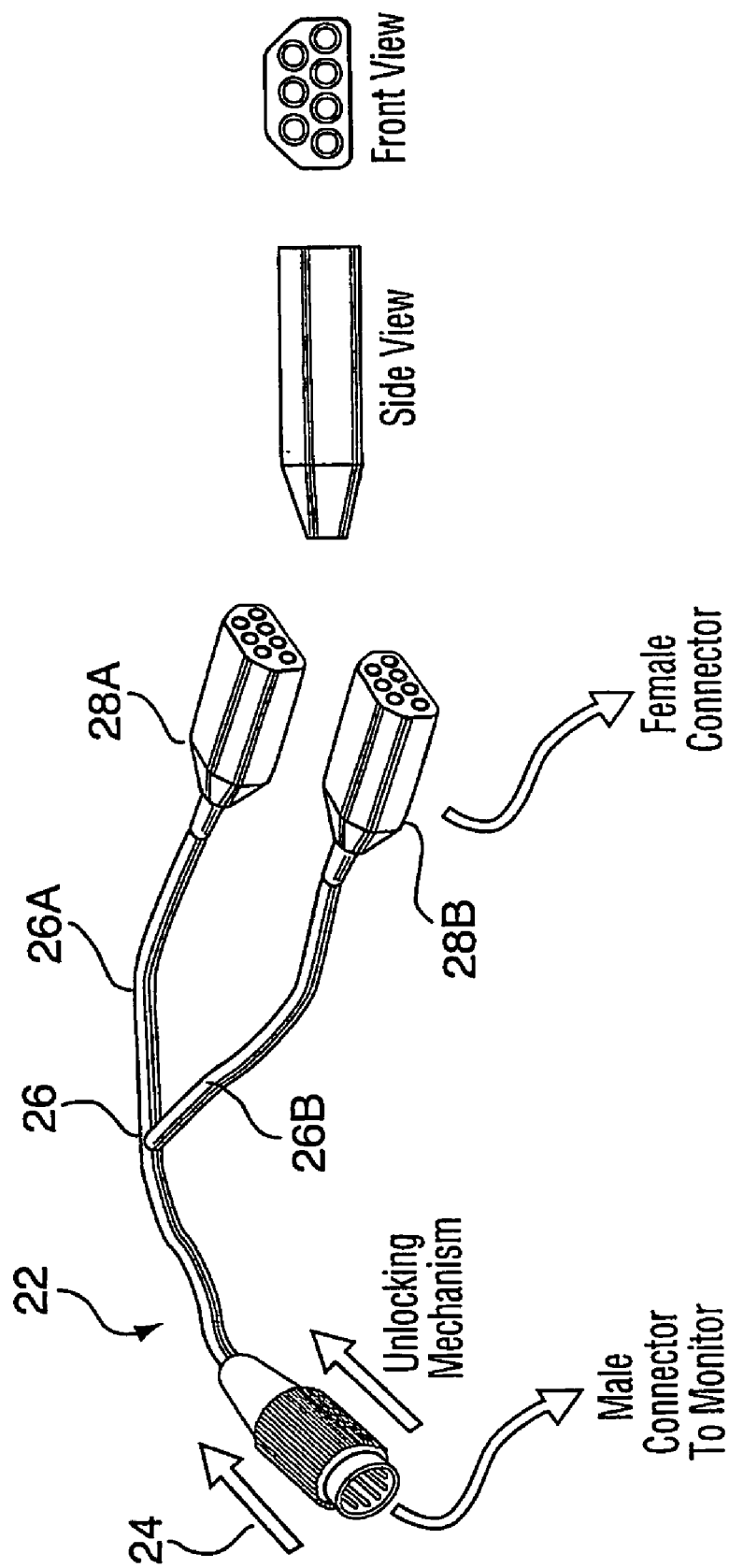
FIG. 1 is an isometric view of a Y-type connector according to the invention.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

The invention relates to a removable sensor which includes a circuit containing information about the sensor. In preferred embodiment the circuit includes a memory capable of being updated with new information. The circuit may comprise a single-chip microcontroller, for example, a model PIC12CE518/9 available from Microchip Technology Inc. of Arizona. The circuit may comprise a memory device, such as a serial electrically erasable PROM memory chip. The memory device could comprise, for example, a model 24AA00/LC00 serial electrically erasable PROM also available from Microchip Technology Incorporated. In some embodiments the sensor may be a disposable sensor or a sensor having a limited life span.

The information contained in the circuit may include information about the sensor itself. For example, the information may include:

information about the manufacturer of the sensor;
information about the model of the sensor;
information about the type of the sensor;
a unique serial number for the sensor;
information about the date of manufacture of the sensor;
information about the intended use of the sensor (e.g. for a pulse-oximetry sensor, information regarding a location on a subject's body at which the sensor is designed to be placed);
calibration information for the sensor;
information about an operational status of the sensor; or,
information about faults in the sensor.

The information may include information regarding uses of the sensor such as:

an indication as to whether the sensor has been used;
an indication as to when the sensor was last serviced or calibrated;
identification of a subject in association with which the sensor has been used (for sensors which are intended for use only with a specific subject and should be thrown away or refurbished before use on another subject);
information about when the sensor was used, or used first;
information about a cumulative length of time during which the sensor was used; or,
information about a number of times that the sensor has been used.

The invention also relates to a system which includes a sensor according to the invention connected to deliver a signal to a monitoring device. The monitoring device may obtain information from the circuit and take actions in response to the received information. Where the sensor is of a disposable type, the information retrieved may relate to previous uses of the sensor. If the information indicates that the sensor's service life is over then the action taken may be to reject the signal from the sensor. If the information indicates that the sensor's service life is not over then, during the use of the sensor the monitoring device may send new information regarding the use of the sensor to be stored by the circuit. The new information may comprise information of one or more of the types described above.

The information retrieved by the monitoring device may also relate to the sensor itself. In cases where the monitoring device requires signals from multiple sensors in order to determine a value for a physiological parameter then the monitoring device may use information received from the circuits on each of the sensors to verify that an appropriate combination of sensors has been connected for the test being conducted. One situation where this capability is useful is in making differential pulse transit time based blood pressure measurements. A system for making such measurements is described in commonly owned international application No. PCT/No. PCT/CA00/01552 filed 22 Dec., 2000 and entitled CONTINUOUS BLOOD PRESSURE MONITORING METHOD AND APPARATUS, which is hereby incorporated by reference herein.

Differential pulse transit time measurements involve detecting the arrival of a pulse wave at different locations on a subject's body. There is a correlation between the difference between the times at which the pulse wave is detected at the two locations and the subject's blood pressure. Differential pulse transit time based blood pressure measurements generally require sensors to be located at different locations on a subject's body. The two sensors may, for example, each be located at different locations selected from the subject's:

forehead;
ear lobe;
fingertip;
toe;
femoral artery; etc.

Typically sensors designed for each of these locations have a different configuration. The calibration of the monitoring device will depend upon which pair of locations is chosen for the sensors.

Where the sensors being used are equipped with information-containing circuits according to this invention then the monitoring device can put the information in the circuits on the sensors to use in various ways. The monitoring device may first check to ensure that an appropriate combination of sensors has been selected. For example, if the monitoring devices retrieves from both sensors indicating that the sensors are both of a type adapted for use at the same location then the monitoring device may generate a warning indication or may refuse to operate.

In some cases a monitoring device may be calibrated to determine the blood pressure of a particular subject for two or more different pairs of sensor locations. For example, the monitoring device may maintain a first set of calibration information which correlates pulse signals detected at the subject's ear lobe and fingertip to the subject's blood pressure and a second set of calibration information which correlates pulse signals detected at the subject's earlobe and toe to the subject's blood pressure. By retrieving information from each of the sensors regarding the location at which the sensor is designed to be used the monitoring device can verify that it has calibration information for that pair of sensor locations and can select for use the calibration information appropriate for the pair of sensors being used.

While the invention also has application to other types of sensors it has particular application to sensors of the type used for pulse oximetry. Pulse oximetry sensors are commonly used to measure the oxygen saturation of a subject's blood and also to measure a subject's pulse rate.

A typical pulse sensor typically comprises one or more (most typically two or more) light sources. The light sources may comprise light-emitting diodes, and a light detector, such as a phototransistor or photodiode. The photo-transistor detects light which is either passed through a fold of the subject's skin or has been reflected from the subject's skin. A signal detected by the photo-transistor (or other light detector) is returned to an analysis circuit in a monitoring device. The monitoring device determines from the signal values of physiological parameters such as pulse rate and blood oxygen saturation.

In monitoring systems which makes use of multiple sensors there are more points at which faults can occur. Diagnosing such faults is more difficult in a device which has multiple sensors than it is in a device, such as a simple pulse oximetry system, which has only a single sensor. The information circuit of the invention may comprise circuitry for detecting common faults in the sensor with which it is associated. This provides useful capabilities for pinpointing defective sensors.

The sensor may comprise a timer. The timer may be integrated with the information containing circuit or may be separate. The timer may track a duration in which the sensor is in use. Where the information containing circuit comprises a microprocessor the timer may comprise a clock associated with the microprocessor. In the alternative, the timer may comprise a separate timing circuit. The information containing circuit may comprise a memory location 19A storing a current timer value. The current timer value is updated in response to signals from the timer.

Memory location 19A may be in a persistent memory. This is not necessary for all applications.

The timer may track the duration of events of significance to the sensor. For example, the timer may track one or more of:

a cumulative time during which the sensor has been "on";
a cumulative time during which an active component in the sensor has been operating;
a cumulative time during which the sensor has been acquiring data from a subject; and,
a cumulative time since an event, such as a sensor reset, a sensor error, the sensor was calibrated, an interruption in a signal detected by the sensor, an unusual signal condition, or the like.

Figure 2:
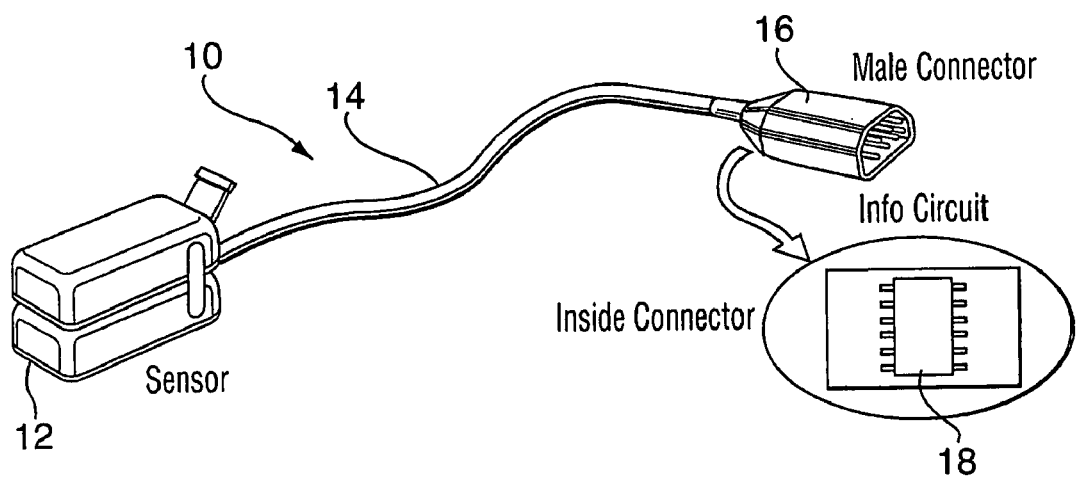
FIG. 2 is an isometric view of a sensor which may be connected to the Y-type connector of FIG. 1.

As shown in FIG. 2, a sensor assembly 10 according to one embodiment of the invention comprises a sensor 12, a cord 14 and a connector 16 for connecting the sensor directly or indirectly to a monitoring device. An information circuit 18 is incorporated into the sensor. In the illustrated embodiment, information circuit 18 comprises a chip built into connector 16. In the illustrated embodiment, information circuit 18 comprises a timer 19.

When sensor assembly 10 is connected to a monitoring device 20 by way of connector 16 (See FIG. 4) the information circuit is able to communicate with the monitoring device. Communication between the information circuit 18 and the monitoring device may be carried, for example, by conductors in connector 16. The conductors may comprise optical fibers, electrical conductors or other media capable of carrying information between information circuit 18 and a monitoring device.

Sensor assembly 10 may be connected directly to monitoring device 20 (if monitoring device 20 has connectors capable of mating with connector 16) or may comprise a suitable extension cable extending between connector 16 and monitoring device 20. Especially where sensor assembly 10 is of a type which is intended to be disposable, it can be desirable to use an extension cable so that the segment 14 of cable in the disposable portion of sensor assembly 10 is relatively short.

FIG. 1 shows an example of a possible extension and adapter cable 22. Cable 22 has a first connector 24 which mates with a connector on monitoring device 20. A cable 26 which has branches 26A and 26B carries signal conductors to second connectors 28A and 28B (collectively connectors 28). Connectors 28 are configured to mate with connectors 16 on sensor assemblies 10. An extension and adapter cable for use in systems according to the invention may have one, two, three or more branches each bearing a connector 28.

Figure 3:
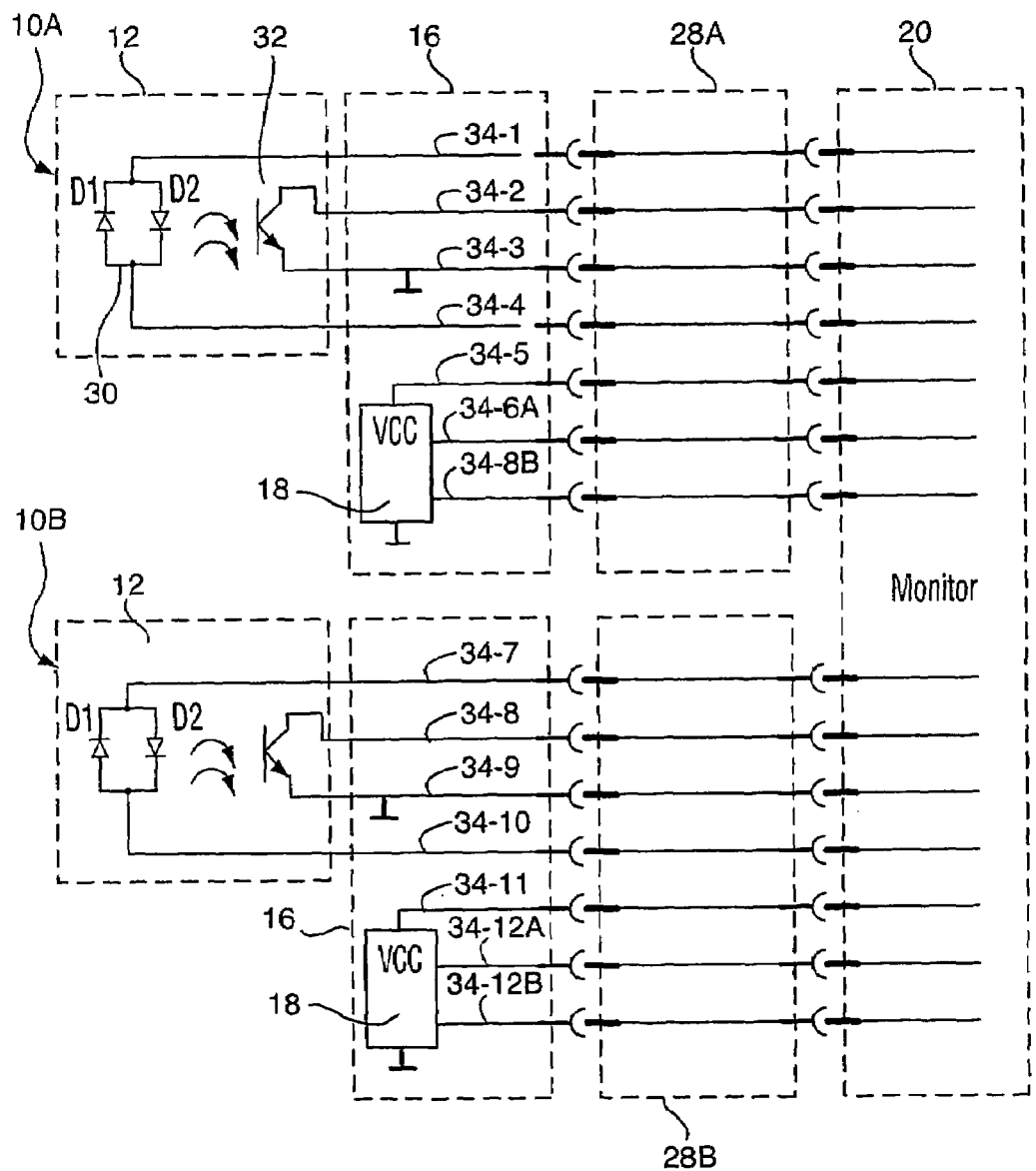
FIG. 3 is a circuit diagram of an assembly comprising the connector of FIG. 1 connected to a pair of sensors similar to those shown in FIG. 2; and, FIG. 4 is a schematic view of a system including a monitoring device according to the invention and a sensor according to the invention.

FIG. 3 is a circuit diagram showing data and power connectors in a system according to the invention which includes a pair of sensor assemblies 10, a Y-type connector cable 22 and a monitoring device 20. In this example embodiment of the invention each sensor 10 comprises a light emitter 30 (which may comprise light-emitting diodes (LEDs)) and a phototransistor or photodiode 32. Conductors 34-1 through 34-12B carry signals to and from monitoring device 20 and carry electrical power to sensor assemblies 10. Conductors 34-2 and 34-3 carry a signal from a first one 10A of the sensor assemblies to monitoring device 20. Conductors 34-8 and 34-9 carry signals from a second one 10B of the sensor assemblies to monitoring device 10.

In this embodiment each information circuit 18 comprises a programmed microcontroller which has an integrated program memory, an integrated timer 19 and an integrated non-volatile memory capable of storing information regarding the sensor assembly 10 and/or the use history of the sensor assembly 10. Monitoring device 20 maintains bidirectional communication with the information circuit 18 associated with first sensor assembly 10A through conductor 34-6A and 34-6B. Monitoring device 20 maintains bidirectional communication with the information circuit 18 associated with second sensor assembly 10B through conductors 34-12A and 34-12B. In the illustrated embodiment, information and commands for circuit 18 are carried serially. In other embodiments of the invention one or more separate data lines may be provided for communication in each direction. Information may also be exchanged between an information circuit 18 and a monitoring device 20 in parallel fashion.

It is a matter of design choice as to whether circuit 18 is configured to send only specific information to monitoring device 18 in response to requests for that specific information from monitoring device 20 or whether in response to a request for information from monitoring device 20, information circuit 18 automatically sends multiple items of information to monitoring device 20. In the latter case, monitoring device 20 can sort through the information retrieved from information circuit 18 to obtain any specific item(s) of information that it requires. Circuit 18 could also, or in the alternative, make periodic transmissions of information to monitoring device 20.

Information circuit 18 may be connected (or selectively connectable) to test points in the associated sensor 12 so that information circuit 18 can obtain information about the normal operation of sensor 12 and/or information that may be relevant to the existence of faults in sensor 12. Information circuit 18 may perform diagnostic checks of sensor 12 and/or provide to monitoring device 20 information useful for conducting diagnostic checks of sensor 12.

Figure 4:
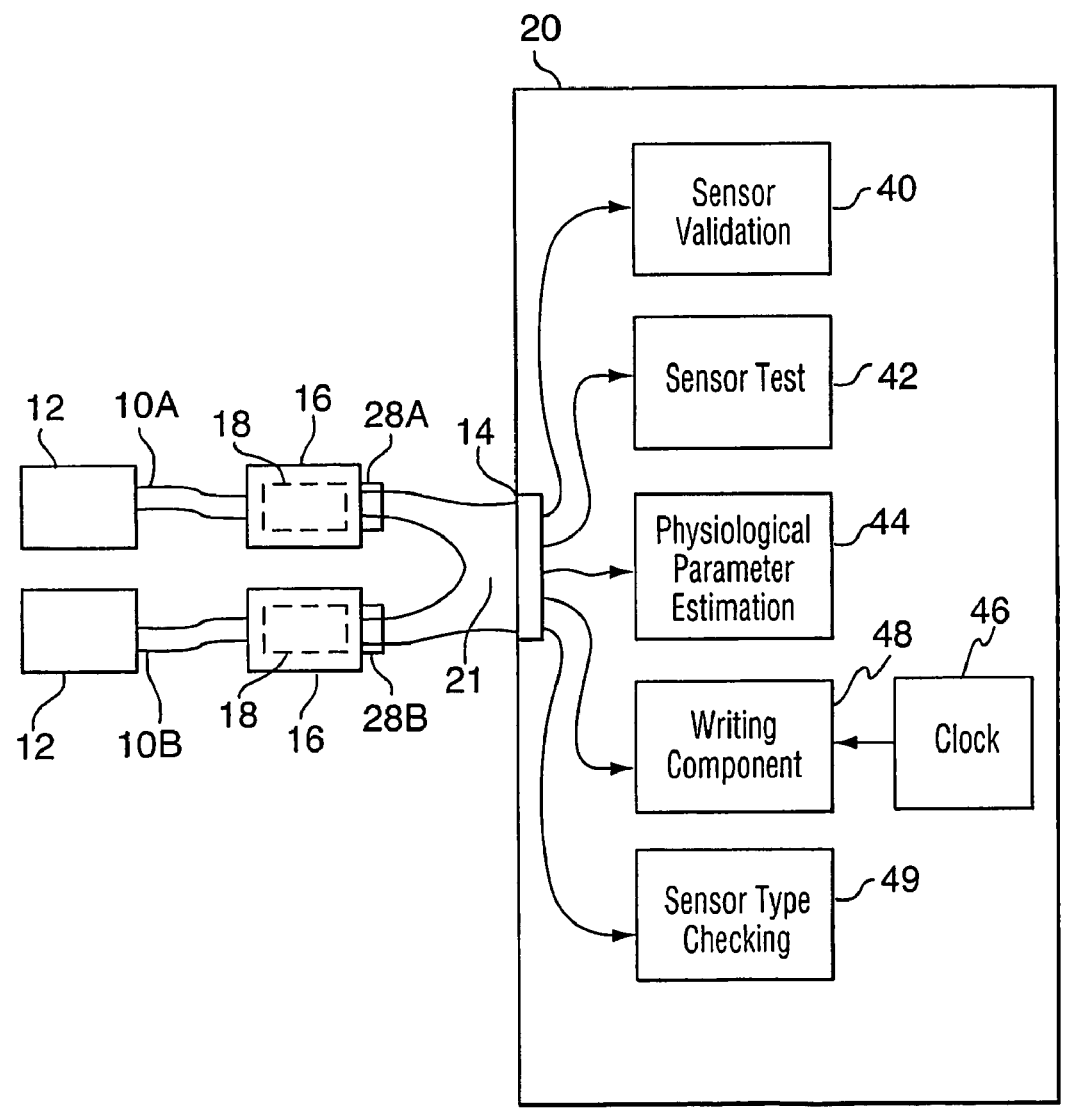

As shown schematically in FIG. 4, monitoring device 20 may comprise a number of functional aspects which interact with information circuits 18 in connected sensor assemblies 10. These functional aspects may be provided in software instructions executed by a programmed data processor, in hardware, or in a combination of hardware and software. The functional aspects are not necessarily separate and distinct from one another in that components for providing one function may also be used by components for providing other functions.

In the embodiment illustrated in FIG. 4, monitoring device 20 comprises a sensor validation function 40. Sensor validation function 40 retrieves information regarding previous usage of sensor assemblies 10 from information circuits 18 and determines if the service life of any one of sensors has been exceeded. This determination may be based upon:

whether the information from information circuit 18 indicates that the sensor assembly has been previously used—for example, for sensor assemblies designed for single use;

whether a cumulative service life exceeds a threshold value (the threshold value may be included in information stored in information circuit 18 and forwarded to monitoring device 20, the comparison may be performed at information circuit 18 and/or the threshold value may be stored in monitoring device 20)(the cumulative service life may comprise one or more of, or a combination of—a time that the sensor has been energized, a time that an active component of the sensor has been energized, a time since the sensor was first used, a time during which the sensor has detected a signal from a subject, and the like)—for example, for sensor assemblies that tend to exhibit degraded performance as they are used;

whether a lifespan has been exceeded from the time that the sensor assembly 10 was first used or manufactured—for example, for sensor assemblies 10 which tend to exhibit performance which degrades with time whether or not the sensor assembly is being used;

whether an excessive time has passed since the sensor assembly 10 was last calibrated;

and so on.

Monitoring device 20 includes a sensor testing function 42. Sensor testing function 42 tests sensor assemblies 10 for faults by either testing directly signals received from sensor assemblies 10, retrieving information about fault conditions from information circuits 18 or both. Where sensor assemblies 10 include a timer 19, sensor testing function 42 may periodically retrieve a value from memory location 19A to verify that timer 19 is operating correctly. For example, sensor testing function 42 may store a value previously retrieved from memory location 19A. When sensor testing function 42 receives a new value from memory location 19A it can compare a difference between the new and previous values to a length of time between acquisition of the new and previous values to verify that timer 19 is functioning properly.

Where memory location 19A comprises a value which represents an amount of time during which a certain component of sensor assembly 10 has been energized then sensor testing function 42 may cause monitoring system 20 to energize the component for a period of time and compare the values stored in memory location 19A before and after the component was energized to verify that timer 19 is accurately tracking the time during which the component is energized.

Monitoring device 20 includes physiological parameter estimation component 44 which receives signals from one or more sensor assemblies 10 and derives estimates of the physiological parameters of a subject from those signals. By way of example only, component 44 may determine a subject's pulse rate, blood oxygen saturation, and/or blood pressure.

Monitoring device 20 includes a clock/calendar component 46 which maintains a record of the current time and date. A writing component 48 sends information to an information circuit 18 for recording in a memory associated with information circuit 18. The information may include the date and time that the sensor assembly 10 associated with the information circuit 18 is being used and the duration of the use.

Monitoring device 20 includes a sensor-type checking component 49. Sensor type checking component 49 obtains information from information circuits 18 regarding the types of sensors connected to monitoring device 20 and verifies that those types of sensor match a function to be performed by physiological parameter estimation component 44. Sensor type-checking component may pass information regarding the types of connected sensors to physiological parameter estimation component 44. By way of example only, physiological parameter estimation component 44 may use this information to configure itself to estimate a physiological parameter for a subject based on signals expected to be received from sensors identified by sensor type-checking component 49.

For example sensor type checking component 49 may determine that the particular sensors connected to monitoring device 20 are for use by a particular known subject. Further, example sensor type checking component 49 may determine that the sensors in question are an earlobe sensor and a fingertip sensor. Physiological parameter estimation component 44 configures itself in response to receiving this information by selecting calibration information for the known subject corresponding to the use of an earlobe and fingertip sensor.

Monitoring device 20 may include a display which displays information retrieved from information circuits 18. The display may, for example, display the types of sensors detected and the name of the subject associated with the sensors. An operator can use the displayed information to check that a procedure is being performed properly on the correct subject.

EXAMPLE

In an example embodiment of the invention, a sensor assembly 10 comprises a pulse oximetry sensor. A clinician wishes to use a sensor assembly 10 to monitor some physiological parameter of a subject. The clinician connects the sensor assembly 10 to a monitoring device 20. Sensor assembly 10 comprises an information circuit 18. Upon sensor assembly 10 being made operational, (for example, upon connection to monitoring device 20, upon monitoring device 20 being turned on, or upon monitoring device 20 energizing sensor assembly 10) monitoring device 20 receives information from information circuit 18. In this example, the information comprises information regarding the type and model number of the sensor, the date of manufacture, the cumulative use time of the sensor, and the cumulative "on" time of a light emitting device in the sensor. In this example, information circuit 18 comprises a microprocessor which, upon being powered up performs a sensor initialization routine which includes instructions which, when executed by the microprocessor, cause the microprocessor to retrieve from a storage location on sensor assembly 10 and forward to a connected monitoring device 20 the information.

Monitoring device 20 performs a monitor initialization routine upon connection of sensor assembly 10. The monitor initialization routine may be performed periodically after sensor assembly 10 has been connected. The monitor initialization routine performs a number of checks on the information. In this example, the monitor initialization routine completes successfully if:

the date of manufacture of the sensor is longer before a current date maintained in the monitoring system than a threshold time;

the cumulative use time of the sensor does not exceed a threshold amount;

the cumulative "on" time of a light emitting device in the sensor does not exceed a threshold amount;

the information is consistent with information previously recorded in monitoring device 20 and associated with the unique serial number for the sensor.

If the monitor initialization routine does not complete successfully then monitoring device 20 signals an error.

While sensor assembly 10 is operational (for example, while monitoring device 20 is applying power to sensor assembly 10) information circuit 18 periodically updates and stores in a memory location of sensor assembly 10 the cumulative use time. Information circuit 18 also monitors whether or not the light emitting device is energized and stores in another memory location the cumulative "on" time of the light emitting device. Information circuit 18 periodically sends information about the cumulative use time to monitoring device 20.

Monitoring device 20 uses the information about the cumulative use time to check the operation of the timer function of sensor assembly 10 as described above. If the check indicates that the timer function is not operating properly then monitoring device 20 signals an error.

During use information circuit 18 monitors various aspects of the operation of the sensor. Information circuit 18 may send status information periodically back to monitoring device 20. If the status information indicates a sensor failure, or if monitoring device 20 fails to receive the status information for a time which is longer than a threshold time then monitoring device 20 signals an error.

Sensor assembly 10 acquires a signal from a subject. The signal passes to monitoring device 20 for analysis.

As will be apparent to those skilled in the art in tie light of the foregoing disclosure, many alterations and modifications are possible in the practice of this invention without departing from the spirit or scope thereof. For example, a single sensor assembly may comprise multiple sensors. Where this is the case a single information circuit may be provided for the sensor assembly. The different sensors and information circuits connected to a monitoring device 20 may share common power circuits, ground connections and the like in ways which are consistent with maintaining acceptable signal quality. The foregoing description includes many features which may be used in the combinations described above, in other combinations or individually.

What is claimed is:

1. A system for determining a value of a physiological parameter, the system comprising a detachable sensor assembly for supplying a signal to a device for monitoring a physiological parameter of a subject, the detachable sensor assembly comprising:

a sensor;

an information containing circuit;

a timer; and, a connector comprising one or more signal conductors connected to carry information from the sensor and information from the information containing circuit to a device for monitoring a physiological parameter;

wherein the information containing circuit is configured to store time-varying information in response to timing signals from the timer and to transmit the time varying information by way of the connector;

wherein the time-varying information comprises a cumulative use time for a component comprising a light-emitting element in the detachable sensor assembly the sensor assembly connected by way of the connector to a monitoring device;

wherein the monitoring device is configured to:

retrieve a first instance of a time-varying value from the information containing circuit at a first time;

store the first instance of the time-varying value in a memory;

retrieve a second instance of the time-varying value from the information containing circuit at a second time later than the first time;

compare the first and second instances of the time-varying value to a difference between the first and second times;

energize the component at or before the first time;

retrieve from the information containing circuit information identifying a date of manufacturing the detachable sensor assembly;

compare the date of manufacture to a current date maintained in the monitoring device; and, signal an error if the date of manufacture of the sensor assembly is longer before the current date than a threshold time;

retrieve from the information containing circuit information identifying a cumulative use time of the detachable sensor assembly;

signal an error if the cumulative use time exceeds a threshold;

retrieve from the information containing circuit information identifying a cumulative on time of the component in the detachable sensor assembly;

signal an error if the cumulative on time exceeds a threshold;

retrieve information from the information containing circuit;

compare the retrieved information to information stored in the monitoring device which was previously retrieved from the information containing circuit; and, signal an error if the retrieved information is not consistent with the stored information;

wherein the monitoring device comprises a data store holding stored information identifying one or more acceptable sensor combinations, each of the acceptable sensor combinations comprising a plurality of sensor locations required for the determination of a physiological parameter; and, a plurality of sensors including said sensor, each detachably connected to the monitoring device, each of the sensors intended for application to a different location on a subject's anatomy, each of the sensors comprising a circuit containing stored information indicating the intended location for the sensor;

wherein the monitoring device comprises a processor connected to retrieve the stored information from each of the plurality of sensors, and to determine from the retrieved stored information whether the plurality of sensors includes all sensors of at least one of the acceptable sensor combinations.

2. A system according to claim 1 wherein the monitoring device comprises stored calibration information corresponding to each of the acceptable sensor combinations and the processor is configured to determine a value for the physiological parameter by applying the calibration information corresponding to the identified acceptable sensor combination to process signals from a plurality of the plurality of sensors corresponding to the identified acceptable sensor combination.

3. A system according to claim 2 wherein the physiological parameter comprises a blood pressure.

4. A system according to claim 3 wherein the sensors each comprise a pulse oximetry sensor.

5. Apparatus for monitoring a physiological parameter of a subject, the apparatus comprising:
- a monitoring device comprising stored information identifying one or more acceptable sensor combinations, each of the acceptable sensor combinations comprising a plurality of sensor locations required for the determination of a physiological parameter; and,
- a plurality of sensors detachably connected to the monitoring device, each of the sensors intended for application to a different location on a subject's anatomy, each of the sensors comprising a circuit containing stored information indicating the intended location for the sensor;
- wherein the monitoring device comprises a processor connected to retrieve the stored information from each of the plurality of sensors, and to determine from the retrieved stored information whether the plurality of sensors includes all sensors of at least one of the acceptable sensor combinations.

6. The apparatus of claim 5 wherein the monitoring device comprises stored calibration information corresponding to each of the acceptable sensor combinations and the processor is configured to determine a value for the physiological parameter by applying the calibration information corresponding to the identified acceptable sensor combination to process signals from a plurality of the plurality of sensors corresponding to the identified acceptable sensor combination.

7. The apparatus of claim 6 wherein the physiological parameter comprises a blood pressure.

8. The apparatus of claim 7 wherein the sensors each comprise a pulse oximetry sensor.

9. A system for determining a value of a physiological parameter, the system comprising a detachable sensor assembly for supplying a signal to a device for monitoring a physiological parameter of a subject, the detachable sensor assembly comprising:
- a sensor;
- an information containing circuit;
- a timer; and,
- a connector comprising one or more signal conductors connected to carry information from the sensor and information from the information containing circuit to a device for monitoring a physiological parameter;
- wherein the information containing circuit is configured to store time-varying information in response to timing signals from the timer and to transmit the time varying information by way of the connector;
- wherein the monitoring device comprises a data store holding stored information identifying one or more acceptable sensor combinations, each of the acceptable sensor combinations comprising a plurality of sensor locations required for the determination of a physiological parameter; and,
- a plurality of sensors including said sensor, each detachably connected to the monitoring device, each of the sensors intended for application to a different location on a subject's anatomy, each of the sensors comprising a circuit containing stored information indicating the intended location for the sensor;
- wherein the monitoring device comprises a processor connected to retrieve the stored information from each of the plurality of sensors, and to determine from the retrieved stored information whether the plurality of sensors includes all sensors of at least one of the acceptable sensor combinations.

10. A system according to claim 9 wherein the information containing circuit comprises a microprocessor.

11. A system according to claim 10 wherein the timer comprises a clock of the microprocessor.

12. A system according to claim 9 wherein the sensor comprises a pulse oximetry sensor.

13. A system according to claim 9 wherein the information containing circuit comprises stored information comprising one or more of:
- information identifying a manufacturer of the detachable sensor assembly;
- information identifying a model of the detachable sensor assembly;
- information identifying a type of the detachable sensor assembly;
- a unique serial number for the detachable sensor assembly;
- information identifying a date of manufacture of the detachable sensor assembly;
- information identifying a location on a subject's body at which the sensor is intended to be placed; and,
- calibration information for the sensor.

14. A system according to claim 9 wherein the information containing circuit is configured to transmit the time varying information in response to a request signal received by way of the connector.

15. A system according to claim 9 wherein the information containing circuit is configured to transmit the time varying information periodically in response to a timing signal from the timer.

16. A system according to claim 9 wherein the information containing circuit comprises a non-volatile memory.

17. A system according to claim 9 wherein the monitoring device is configured to:
- retrieve a first instance of the time varying value from the information containing circuit at a first time;
- store the first instance of the time varying value in a memory;
- retrieve a second instance of the time varying value from the information containing circuit at a second time later than the first time; and,
- compare the first and second instances of the time varying value to a difference between the first and second times.

18. A system according to claim 17 wherein the time varying value comprises a cumulative use time for a component in the detachable sensor assembly and the monitoring device is configured to energize the component at or before the first time.

19. A system according to claim 18 wherein the monitoring device is configured to:
- retrieve from the information containing circuit information identifying a date of manufacturing the detachable sensor assembly;
- compare the date of manufacture to a current date maintained in the monitoring device; and,
- signal an error if the date of manufacture of the sensor assembly is longer before the current date than a threshold time.

20. A system according to claim 19 wherein the monitoring device is configured to:
- retrieve from the information containing circuit information identifying a cumulative use time of the detachable sensor assembly; and signal an error if the cumulative use time exceeds a threshold.

21. A system according to claim 20 wherein the monitoring device is configured to:

retrieve from the information containing circuit information identifying a cumulative on time of a component in the detachable sensor assembly; and, signal an error if the cumulative on time exceeds a threshold.

22. A system according to claim 21 wherein the component comprises a light emitting element.

* * * * *